(12) United States Patent
Waitkus et al.

(10) Patent No.: US 11,938,277 B2
(45) Date of Patent: Mar. 26, 2024

(54) CATHETERIZATION SYSTEM AND METHODS FOR USE THEREOF

(71) Applicant: C. R. Bard, Inc., Franklin Lakes, NJ (US)

(72) Inventors: Tim Waitkus, Sparta, NJ (US); Chris Fodouop, Atlanta, GA (US); Kelsey Leeke, Atlanta, GA (US); John Gohde, Decatur, GA (US); Logan Madden, Covington, LA (US); Nichole Abla, Atlanta, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 59 days.

(21) Appl. No.: 17/054,493

(22) PCT Filed: May 21, 2019

(86) PCT No.: PCT/US2019/033389
§ 371 (c)(1),
(2) Date: Nov. 10, 2020

(87) PCT Pub. No.: WO2019/226697
PCT Pub. Date: Nov. 28, 2019

(65) Prior Publication Data
US 2021/0187240 A1 Jun. 24, 2021

Related U.S. Application Data

(60) Provisional application No. 62/675,103, filed on May 22, 2018.

(51) Int. Cl.
*A61M 25/00* (2006.01)
*A61M 25/10* (2013.01)
*G16H 10/60* (2018.01)

(52) U.S. Cl.
CPC ........ *A61M 25/0017* (2013.01); *A61M 25/10* (2013.01); *G16H 10/60* (2018.01);
(Continued)

(58) Field of Classification Search
CPC ............ A61M 25/0017; A61M 1/0011; A61M 25/10; A61M 2025/0002; A61M 2205/18;
(Continued)

(56) References Cited

U.S. PATENT DOCUMENTS 3,661,143 A  5/1972  Henkin
3,781,920 A  1/1974  Browne et al.
(Continued)

FOREIGN PATENT DOCUMENTS

CA  2882654 A1  10/2007
CN  2445749 Y  9/2001
(Continued)

OTHER PUBLICATIONS

PCT/US19/33389 filed May 21, 2019 International Search Report and Written Opinion dated Aug. 2, 2019.
(Continued)

*Primary Examiner* — Catharine L Anderson
*Assistant Examiner* — Nhu Q. Tran
(74) *Attorney, Agent, or Firm* — Rutan & Tucker LLP

(57) ABSTRACT

A catheterization system including a catheter, drainage bag and one or more indicators configured to measure an attribute relating to the usage of the catheter system and communicate information about the attribute to a network, such as an EMR database. The indicators may include a location indicator, a duration indicator, an elevation indicator, a tamper indicator, a dependent loop indicator, a floor contact indicator, and a patient securement indicator. The system
(Continued)

Figure 1:
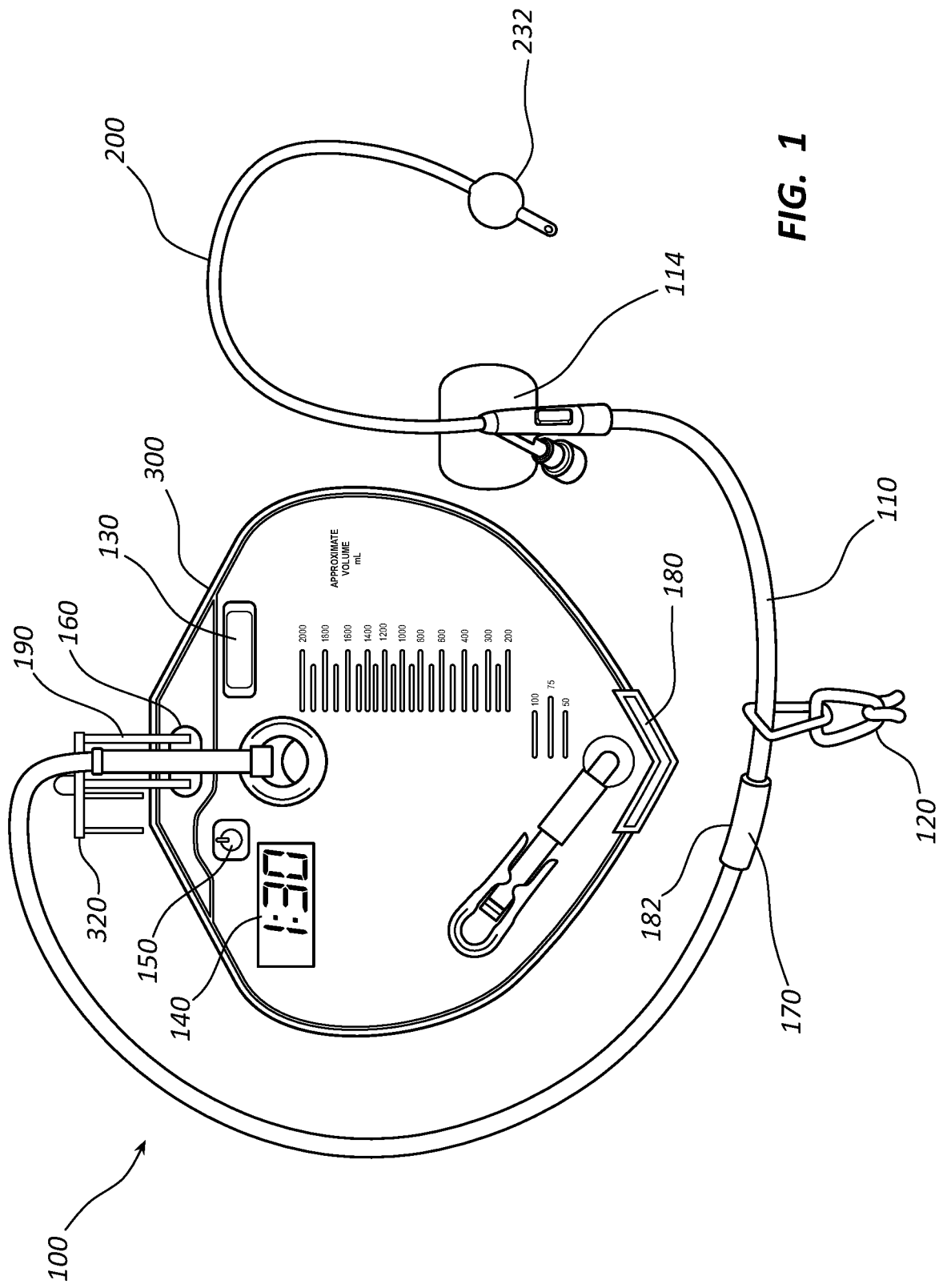

may autonomously detect and record one or more attributes relating to the usage of the catheter system.

11 Claims, 3 Drawing Sheets

(52) U.S. Cl.
CPC . *A61M 2025/0002* (2013.01); *A61M 2205/18* (2013.01); *A61M 2205/33* (2013.01); *A61M 2205/3553* (2013.01)

(58) Field of Classification Search
CPC ...... A61M 2205/33; A61M 2205/3553; A61M 25/04; A61M 27/00; A61B 5/0002; A61B 5/20; A61B 5/6852
See application file for complete search history.

(56) References Cited

U.S. PATENT DOCUMENTS

| | | | |
|---|---|---|---|
| 3,851,650 A | 12/1974 | Darling | |
| 3,919,455 A | 11/1975 | Sigdell et al. | |
| 4,276,889 A | 7/1981 | Kuntz et al. | |
| 4,286,590 A | 9/1981 | Murase | |
| 4,291,692 A | 9/1981 | Bowman et al. | |
| 4,296,749 A | 10/1981 | Pontifex | |
| 4,305,405 A | 12/1981 | Meisch | |
| 4,312,352 A | 1/1982 | Meisch et al. | |
| 4,343,316 A | 8/1982 | Jespersen | |
| 4,443,219 A | 4/1984 | Meisch et al. | |
| 4,448,207 A | 5/1984 | Parrish | |
| 4,509,366 A | 4/1985 | Matsushita et al. | |
| 4,532,936 A | 8/1985 | LeVeen et al. | |
| 4,658,834 A | 4/1987 | Blankenship et al. | |
| 4,723,950 A | 2/1988 | Lee | |
| 4,834,706 A | 5/1989 | Beck et al. | |
| 4,850,375 A | 7/1989 | Rosenberg | |
| 4,889,532 A | 12/1989 | Metz et al. | |
| 5,002,541 A | 3/1991 | Conkling et al. | |
| 5,409,014 A | 4/1995 | Napoli et al. | |
| 5,586,085 A | 12/1996 | Lichte | |
| 5,725,515 A | 3/1998 | Propp | |
| 5,733,319 A | 3/1998 | Neilson et al. | |
| 5,738,656 A | 4/1998 | Wagner | |
| 5,747,824 A | 5/1998 | Jung et al. | |
| 5,769,087 A | 6/1998 | Westphal et al. | |
| 5,807,278 A | 9/1998 | McRae | |
| 5,823,972 A | 10/1998 | McRae | |
| 5,891,051 A | 4/1999 | Han et al. | |
| 5,911,786 A | 6/1999 | Nielsen et al. | |
| 6,129,684 A | 10/2000 | Sippel et al. | |
| 6,132,407 A | 10/2000 | Genese et al. | |
| 6,250,152 B1 | 6/2001 | Klein et al. | |
| 6,256,532 B1 | 7/2001 | Cha | |
| 6,261,254 B1 | 7/2001 | Baron et al. | |
| 6,434,418 B1 | 8/2002 | Neal et al. | |
| 6,579,247 B1 | 6/2003 | Abramovitch et al. | |
| 6,592,612 B1 | 7/2003 | Samson et al. | |
| 6,709,420 B1 | 3/2004 | Lincoln et al. | |
| 6,716,200 B2 | 4/2004 | Bracken et al. | |
| 7,011,634 B2 | 3/2006 | Paasch et al. | |
| 7,161,484 B2 | 1/2007 | Tsoukalis | |
| 7,437,945 B1 | 10/2008 | Feller | |
| 7,442,754 B2 | 10/2008 | Tepper et al. | |
| 7,739,907 B2 | 6/2010 | Boiarski | |
| 7,871,385 B2 | 1/2011 | Levinson | |
| 7,931,630 B2 | 4/2011 | Nishtala et al. | |
| 7,976,533 B2 | 7/2011 | Larsson | |
| 7,998,126 B1 | 8/2011 | Fernandez | |
| 8,295,933 B2 | 10/2012 | Gerber et al. | |
| 8,328,733 B2 | 12/2012 | Forte et al. | |
| 8,328,734 B2 | 12/2012 | Salvadori et al. | |
| 8,337,476 B2 | 12/2012 | Greenwald et al. | |
| 8,374,688 B2 | 2/2013 | Libbus et al. | |
| 8,403,884 B2 | 3/2013 | Nishtala | |
| 8,471,231 B2 | 6/2013 | Paz | |
| 8,663,128 B2 | 3/2014 | Paz et al. | |
| 8,773,259 B2 | 7/2014 | Judy et al. | |
| 8,790,277 B2 | 7/2014 | Elliott et al. | |
| 8,790,320 B2 | 7/2014 | Christensen | |
| 8,790,577 B2 | 7/2014 | Mizumoto et al. | |
| 8,813,551 B2 | 8/2014 | Boiarski | |
| 8,827,924 B2 | 9/2014 | Paz et al. | |
| 8,832,558 B2 | 9/2014 | Cardarelli et al. | |
| 8,900,196 B2 | 12/2014 | Andino | |
| 9,045,887 B2 | 6/2015 | O'Malley | |
| 9,050,046 B2 | 6/2015 | Elliott et al. | |
| 9,074,920 B2 | 7/2015 | Mendels et al. | |
| 9,216,242 B2 | 12/2015 | Nishtala et al. | |
| 9,480,821 B2 | 11/2016 | Ciccone et al. | |
| 9,592,034 B2 | 3/2017 | Hall et al. | |
| 9,642,987 B2 | 5/2017 | Bierman et al. | |
| 9,731,097 B2 | 8/2017 | Andino et al. | |
| 9,895,095 B2 | 2/2018 | Chen | |
| 9,962,516 B2 | 5/2018 | Lampotang et al. | |
| 10,182,747 B2 | 1/2019 | Charlez et al. | |
| 10,245,008 B2 | 4/2019 | Paige | |
| 10,362,981 B2 | 7/2019 | Paz et al. | |
| 10,383,606 B1 | 8/2019 | McCord et al. | |
| 10,448,875 B2 | 10/2019 | Holt et al. | |
| 11,703,365 B2 | 7/2023 | Tourchak et al. | |
| 2001/0056226 A1 | 12/2001 | Zodnik et al. | |
| 2002/0016719 A1 | 2/2002 | Nemeth et al. | |
| 2002/0161314 A1 | 10/2002 | Sarajarvi | |
| 2002/0193760 A1 | 12/2002 | Thompson | |
| 2003/0000303 A1 | 1/2003 | Livingston et al. | |
| 2003/0163183 A1 | 8/2003 | Carson | |
| 2003/0163287 A1 | 8/2003 | Vock et al. | |
| 2004/0267086 A1 | 12/2004 | Anstadt et al. | |
| 2005/0020958 A1 | 1/2005 | Paolini et al. | |
| 2005/0065583 A1 | 3/2005 | Voorhees et al. | |
| 2005/0172712 A1 | 8/2005 | Nyce | |
| 2005/0247121 A1 | 11/2005 | Pelster | |
| 2006/0100743 A1 | 5/2006 | Townsend et al. | |
| 2007/0010797 A1 | 1/2007 | Nishtala et al. | |
| 2007/0145137 A1 | 6/2007 | Mrowiec | |
| 2007/0252714 A1 | 11/2007 | Rondoni et al. | |
| 2008/0312556 A1 | 12/2008 | Dijkman | |
| 2009/0056020 A1 | 3/2009 | Caminade et al. | |
| 2009/0099629 A1 | 4/2009 | Carson et al. | |
| 2009/0157430 A1 | 6/2009 | Rule et al. | |
| 2009/0287170 A1 | 11/2009 | Otto | |
| 2009/0315684 A1 | 12/2009 | Sacco et al. | |
| 2010/0094204 A1 | 4/2010 | Nishtala | |
| 2010/0130949 A1 | 5/2010 | Garcia | |
| 2010/0137743 A1 | 6/2010 | Nishtala et al. | |
| 2011/0113540 A1 | 5/2011 | Plate et al. | |
| 2011/0120219 A1 | 5/2011 | Barlesi et al. | |
| 2011/0178425 A1 | 7/2011 | Nishtala et al. | |
| 2011/0238042 A1 | 9/2011 | Davis et al. | |
| 2011/0251572 A1 | 10/2011 | Nishtala et al. | |
| 2011/0263952 A1 | 10/2011 | Bergman et al. | |
| 2012/0029408 A1 | 2/2012 | Beaudin | |
| 2012/0059286 A1* | 3/2012 | Hastings | A61B 18/1206 601/2 |
| 2012/0078137 A1 | 3/2012 | Mendels et al. | |
| 2012/0078235 A1* | 3/2012 | Martin | A61M 25/0017 604/544 |
| 2012/0095304 A1 | 4/2012 | Biondi | |
| 2012/0109008 A1 | 5/2012 | Charlez et al. | |
| 2012/0123233 A1 | 5/2012 | Cohen | |
| 2012/0127103 A1 | 5/2012 | Qualey et al. | |
| 2012/0226196 A1 | 9/2012 | DiMino et al. | |
| 2012/0234434 A1 | 9/2012 | Woodruff et al. | |
| 2012/0302917 A1 | 11/2012 | Fitzgerald et al. | |
| 2012/0323502 A1 | 12/2012 | Tanoura et al. | |
| 2013/0066166 A1* | 3/2013 | Burnett | A61B 5/14539 600/301 |
| 2013/0109927 A1 | 5/2013 | Menzel | |
| 2013/0109928 A1 | 5/2013 | Menzel | |
| 2013/0131610 A1 | 5/2013 | Dewaele et al. | |
| 2013/0218106 A1 | 8/2013 | Coston et al. | |
| 2013/0245498 A1 | 9/2013 | Delaney et al. | |

(56) References Cited

U.S. PATENT DOCUMENTS

| | | |
|---|---|---|
| 2013/0267871 A1 | 10/2013 | Delaney et al. |
| 2014/0039348 A1 | 2/2014 | Bullington et al. |
| 2014/0155781 A1 | 6/2014 | Bullington et al. |
| 2014/0155782 A1 | 6/2014 | Bullington et al. |
| 2014/0159921 A1 | 6/2014 | Qualey et al. |
| 2014/0207085 A1 | 7/2014 | Brandt et al. |
| 2014/0243635 A1 | 8/2014 | Arefieg |
| 2014/0335490 A1 | 11/2014 | Baarman et al. |
| 2015/0343173 A1* | 12/2015 | Tobescu ............ A61M 25/0017 604/246 |
| 2015/0359522 A1 | 12/2015 | Recht et al. |
| 2015/0362351 A1 | 12/2015 | Joshi et al. |
| 2016/0051176 A1 | 2/2016 | Ramos et al. |
| 2016/0183819 A1 | 6/2016 | Burnett et al. |
| 2017/0100068 A1 | 4/2017 | Kostov |
| 2017/0196478 A1* | 7/2017 | Hunter ............... A61B 5/02055 |
| 2017/0202698 A1 | 7/2017 | Zani et al. |
| 2017/0249445 A1 | 8/2017 | Devries et al. |
| 2017/0290540 A1 | 10/2017 | Franco |
| 2017/0291012 A1 | 10/2017 | Iglesias |
| 2017/0307423 A1 | 10/2017 | Pahwa et al. |
| 2018/0015251 A1 | 1/2018 | Lampotang et al. |
| 2018/0280236 A1 | 10/2018 | Ludin et al. |
| 2018/0344234 A1* | 12/2018 | McKinney ............. A61B 5/205 |
| 2019/0046102 A1 | 2/2019 | Kushnir et al. |
| 2019/0069830 A1 | 3/2019 | Holt et al. |
| 2019/0126006 A1 | 5/2019 | Rehm et al. |
| 2019/0201596 A1 | 7/2019 | Luxon et al. |
| 2019/0223844 A1 | 7/2019 | Aboagye et al. |
| 2019/0247236 A1 | 8/2019 | Sides et al. |
| 2019/0321588 A1 | 10/2019 | Burnett et al. |
| 2019/0328945 A1 | 10/2019 | Analytis et al. |
| 2019/0358387 A1 | 11/2019 | Elbadry et al. |
| 2019/0365308 A1 | 12/2019 | Laing et al. |
| 2019/0381223 A1 | 12/2019 | Culbert et al. |
| 2020/0085378 A1 | 3/2020 | Burnett et al. |
| 2020/0268303 A1 | 8/2020 | Oliva |
| 2020/0289749 A1 | 9/2020 | Odashima et al. |
| 2021/0077007 A1 | 3/2021 | Jouret et al. |
| 2022/0018692 A1 | 1/2022 | Tourchak et al. |
| 2022/0026001 A1 | 1/2022 | Cheng et al. |
| 2022/0026261 A1 | 1/2022 | Funnell et al. |
| 2022/0192564 A1 | 6/2022 | Kriscovich et al. |
| 2022/0192565 A1 | 6/2022 | Cheng et al. |
| 2022/0192566 A1 | 6/2022 | Cheng et al. |
| 2022/0193375 A1 | 6/2022 | Rehm et al. |
| 2022/0296140 A1 | 9/2022 | Nguyen et al. |
| 2022/0386917 A1 | 12/2022 | Mann et al. |
| 2023/0022547 A1 | 1/2023 | Cho et al. |
| 2023/0025333 A1 | 1/2023 | Patel et al. |
| 2023/0028966 A1 | 1/2023 | Franano |
| 2023/0035669 A1 | 2/2023 | Raja et al. |
| 2023/0040915 A1 | 2/2023 | Compton et al. |
| 2023/0058553 A1 | 2/2023 | Fallows et al. |
| 2023/0060232 A1 | 3/2023 | Patel et al. |
| 2023/0084476 A1 | 3/2023 | Robichaud et al. |

FOREIGN PATENT DOCUMENTS

| | | |
|---|---|---|
| CN | 200951235 Y | 9/2007 |
| CN | 201492414 U | 6/2010 |
| CN | 102647939 A | 8/2012 |
| CN | 109498013 A | 3/2019 |
| CN | 110859636 A | 3/2020 |
| CN | 112426156 A | 3/2021 |
| EP | 0342028 A2 | 11/1989 |
| ES | 2760470 T3 | 5/2020 |
| GB | 2576743 A | 3/2020 |
| JP | S49-75171 A | 7/1974 |
| JP | S54-147066 A | 11/1979 |
| JP | S58-190719 A | 11/1983 |
| JP | S60-219517 A | 11/1985 |
| JP | H02-057240 B2 | 12/1990 |
| JP | H08-271301 A | 10/1996 |
| JP | H10104041 A | 4/1998 |
| JP | 2007303982 A | 11/2007 |
| JP | 2008-524618 A | 7/2008 |
| JP | 2009-068959 A | 4/2009 |
| JP | 2010-121950 A | 6/2010 |
| JP | 2010-530978 A | 9/2010 |
| JP | 2012-105947 A | 6/2012 |
| JP | 2012-225790 A | 11/2012 |
| WO | 1981003427 A1 | 12/1981 |
| WO | 2004045410 A1 | 6/2004 |
| WO | 2013013782 A2 | 1/2013 |
| WO | 20130178742 A1 | 12/2013 |
| WO | 2014043650 A2 | 3/2014 |
| WO | 2014108690 A1 | 7/2014 |
| WO | 2014135856 A1 | 9/2014 |
| WO | 2014145971 A2 | 9/2014 |
| WO | 2014151068 A2 | 9/2014 |
| WO | 201511402 A1 | 1/2015 |
| WO | 2015105916 A1 | 7/2015 |
| WO | 2015/127390 A1 | 8/2015 |
| WO | 2016177901 A1 | 11/2016 |
| WO | 2017023794 A1 | 2/2017 |
| WO | 2018156624 A1 | 8/2018 |
| WO | 2019/226697 A1 | 11/2019 |
| WO | 2022108589 A1 | 5/2022 |

OTHER PUBLICATIONS

Bard Medical, Criticore Disposables—Non I.C., 3 pages, www.bardmedical.com/products/patienl-moniloring-,ystems/criticore®-system/criticore®-disposables-non-ic/ Jan. 30, 2015.
Bard Medical, Criticore Infection Control Disposables, 3 pages, www.bardmedical.com/patienl-moniloring-,ystems/criticore®-system/criticore®-infection-conlrol-disposables/ Jan. 30, 2015.
Bard Medical, Criticore Monitor, 11 pages, www.bardmedical.com/products/patient-monitoring-systems/criticore®--monitor/ Jan. 30, 2015.
Bard Medical, Urine Meiers, 3 pages, www.bardmedical.com/producls/urological-drainage/urine-collection/urinemeters/Jan. 30, 2015.
Biometrix, Urimetrix, 4 pages, www.biometrixmedical.com/Products/56/Urimetrix%E2%84%A2 Oct. 29, 2014.
Observe Medical, sippi, 3 pages, www.observemedical.com/products.html Oct. 29, 2014.
PCT/US2016/044835 filed Jul. 20, 2016 International Search Report and Written Opinion dated Dec. 16, 2016.
PCT/US2019/045787 filed Aug. 8, 2019 International Preliminary Report on Patentability dated Feb. 16, 2021.
PCT/US2019/045787 filed Aug. 8, 2019 International Search Report and Written Opinion dated Oct. 2, 2019.
U.S. Appl. No. 15/748,107, filed Jan. 26, 2018 Final Office Action dated Dec. 23, 2020.
U.S. Appl. No. 15/748,107, filed Jan. 26, 2018 Final Office Action dated Feb. 7, 2022.
U.S. Appl. No. 15/748,107, filed Jan. 26, 2018 Non-Final Office Action dated Sep. 3, 2021.
U.S. Appl. No. 15/748,107, filed Jan. 26, 2018 Non-Final Office Action dated Sep. 4, 2020.
U.S. Appl. No. 15/748,107, filed Jan. 26, 2018 Notice of Allowance dated Dec. 12, 2022.
U.S. Appl. No. 17/262,080, filed Jan. 21, 2021 Non-Final Office Action dated Apr. 6, 2023.
U.S. Appl. No. 17/3026,821, filed May 3, 2021 Non-Final Office Action dated Jan. 10, 2023.
U.S. Appl. No. 17/373,535, filed Jul. 12, 2021 Non-Final Office Action dated Nov. 9, 2022.
U.S. Appl. No. 17/373,535, filed Jul. 12, 2021 Notice of Allowance dated Feb. 23, 2023.
PCT/US20/61367 filed Nov. 19, 2020 International Search Report and Written Opinion dated Feb. 22, 2021.
U.S. Appl. No. 17/306,821, filed May 3, 2021 Final Office Action dated Jul. 19, 2023.
U.S. Appl. No. 17/556,907, filed Dec. 20, 2021 Restriction Requirement dated May 12, 2023.
DFree Personal—Consumer Product Brochure, 2019.

(56) References Cited

OTHER PUBLICATIONS

DFree Pro Brochure 2019.

Leonhäuser, D et al., "Evaluation of electrical impedance tomography for determination of urinary bladder volume: comparison with standard ultrasound methods in healthy volunteers."—BioMed Engr On-line; 17:95; 2018.

Li, R., et al., "Design of a Noninvasive Bladder Urinary Volume Monitoring System Based on Bio-Impedance."—Engineering; vol. 5; pp. 321-325; 2013.

Reichmuth, M., et al., "A Non-invasive Wearable Bioimpedance System to Wirelessly Monitor Bladder Filling."—Dep. of Health Sciences and Technology—Department of Information Technology and Electrical Engineering ETH Zurich, Zurich, Switzerland—Conference Paper; Mar. 2020.

SECA product catalog, https://us.secashop.com/products/seca-mbca/seca-mbca-514/5141321139, last accessed Sep. 11, 2020.

U.S. Appl. No. 17/262,080, filed Jan. 21, 2021 Final Office Action dated Sep. 11, 2023.

U.S. Appl. No. 17/262,080, filed Jan. 21, 2021 Notice of Allowance dated Oct. 13, 2023.

U.S. Appl. No. 17/306,821, filed May 3, 2021 Advisory Action dated Oct. 3, 2023.

U.S. Appl. No. 17/556,907, filed Dec. 20, 2021 Non-Final Office Action dated Aug. 17, 2023.

EP 23188337.2 filed May 21, 2019 Extended European Search Report dated Dec. 4, 2023.

U.S. Appl. No. 17/373,546, filed Jul. 12, 2021 Non-Final Office Action dated Nov. 1, 2023.

U.S. Appl. No. 17/556,907, filed Dec. 20, 2021 Notice of Allowance dated Dec. 6, 2023.

\* cited by examiner

CATHETERIZATION SYSTEM AND METHODS FOR USE THEREOF

PRIORITY

This application is a U.S. national stage application of International Application No. PCT/US2019/033389, which claims the benefit of priority to U.S. Provisional Patent Application No. 62/675,103, filed May 22, 2018, each of which is incorporated by reference in its entirety into this application.

BACKGROUND

The purpose of a Foley catheter is to drain urine from the bladder for a variety of medical reasons. However, due to the inherent risk of infection associated with Foley catheters, the Centers for Disease Control and Prevention ("CDC") has published a list of recommendations for the maintenance of Foley catheter systems. Hospitals may make every effort to comply with these recommendations, but monitoring nursing compliance can be difficult. Some facilities have implemented daily audits of their patients with Foley catheters, but this takes time away from the many other tasks required of hospital personnel. In addition, patients who typically use Foley catheter systems are very sick and require constant and accurate monitoring of their vital signs, intakes and outputs, and other important bodily functions. Accordingly, there is a need to enhance the function of the Foley catheter system beyond simply draining urine. The apparatus and methods disclosed herein aim to collect real time data on the usage of the Foley catheter systems to assist nurses with the care and maintenance thereof. This would streamline Foley catheter monitoring, facilitate guideline compliance, and reduce the risk of infection to the patient.

SUMMARY

Provided herein in some embodiments is a Foley catheterization system including systems and methods for monitoring the maintenance of the Foley catheterization system. The Foley catheterization system can include a catheter, tubing, a drainage bag, and an indicator. The indicator may include at least one of a location indicator, a duration indicator, an elevation indicator, a tamper indicator, a dependent loop indicator, a floor contact indicator, and a patient securement indicator. The indicator may include a sensor configured to measure an attribute relating to the use of the catheterization system. The indicator may be communicatively coupled with a network. The indicator may be disposed on at least a drainage bag, catheter, or tubing. The catheter may include a sensor disposed adjacent a distal end of the catheter. The attribute may include at least one of a geographical location, a measure of catheter dwell time, an elevation of the drainage bag relative to a bladder of a patient, a fault in the electrical or fluid communication between the catheter, tubing, and drainage bag, a dependent loop in the tubing, a contact between a portion of the catheter system and a floor surface, and a detachment of a portion of the catheter system from the patient.

Also provided herein in some embodiments is a method of using a Foley catheterization system which may include providing a catheterization system having a catheter, a drainage bag, and an indicator, inserting a distal end of the catheter within a bladder of the patient, inflating a balloon disposed adjacent a distal end of the catheter, fluidly connecting the catheter with the drainage bag, and automatically detecting and recording an attribute relating to the use of the catheterization system. The method may further include the attribute relating to the use of the catheterization system having at least one of: recording a geographic location of the catheterization system, recording a dwell time of the catheter, recording an elevation of the drainage bag relative to the bladder of the patient, recording a fault in the integrity of a connection within the catheterization system, recording the presence of a dependent loop between the catheter and the drainage bag, recording a contact between a portion of the catheter system and a floor surface, and recording a detachment between a portion of the catheter system and the patient. The method may further include the indicator communicatively coupled with a network to transmit information relating to the attribute to the network to be accessed by a medical professional. The method may further include the catheterization system being used until an end point is reached, the end point being determined by at least one of a predetermined date and time, a predetermined amount of time having expired, a predetermined amount of fluid having been collected, or a predetermined event or fault being detected. The method may further include the catheterization system providing an alert to the patient or a medical professional.

Also provided herein in some embodiments is a Foley catheter including a catheter body having a proximal end and a distal end, a balloon disposed adjacent a distal end, a drainage lumen extending from distal end to a proximal end, an inflation lumen extending from the balloon to a proximal end, and a sensor disposed adjacent a distal end and communicatively coupled with an indicator disposed adjacent a proximal end. The catheter may further include the sensor and the indicator communicatively coupled by way of a wire disposed in a wall of the catheter body. The catheter may further include the sensor and the indicator communicatively coupled by means of wireless communication. The catheter may further include the sensor designed to detect at least one of temperature, moisture, pressure, or three-dimensional spatial location. The catheter may further include the indicator designed to communicate with the sensor to detect an attribute relating to at least a spatial location, the presence of moisture, the inflation of the balloon, or internal body temperature. The catheter may further include the indicator communicatively coupled with a network.

These and other features of the concepts provided herein may be better understood with reference to the drawings, description, and appended claims.

DRAWINGS

FIG. 1 provides an exemplary embodiment of a catheterization system including a catheter, tubing, and drainage bag in accordance with some embodiments.

Figure 2:
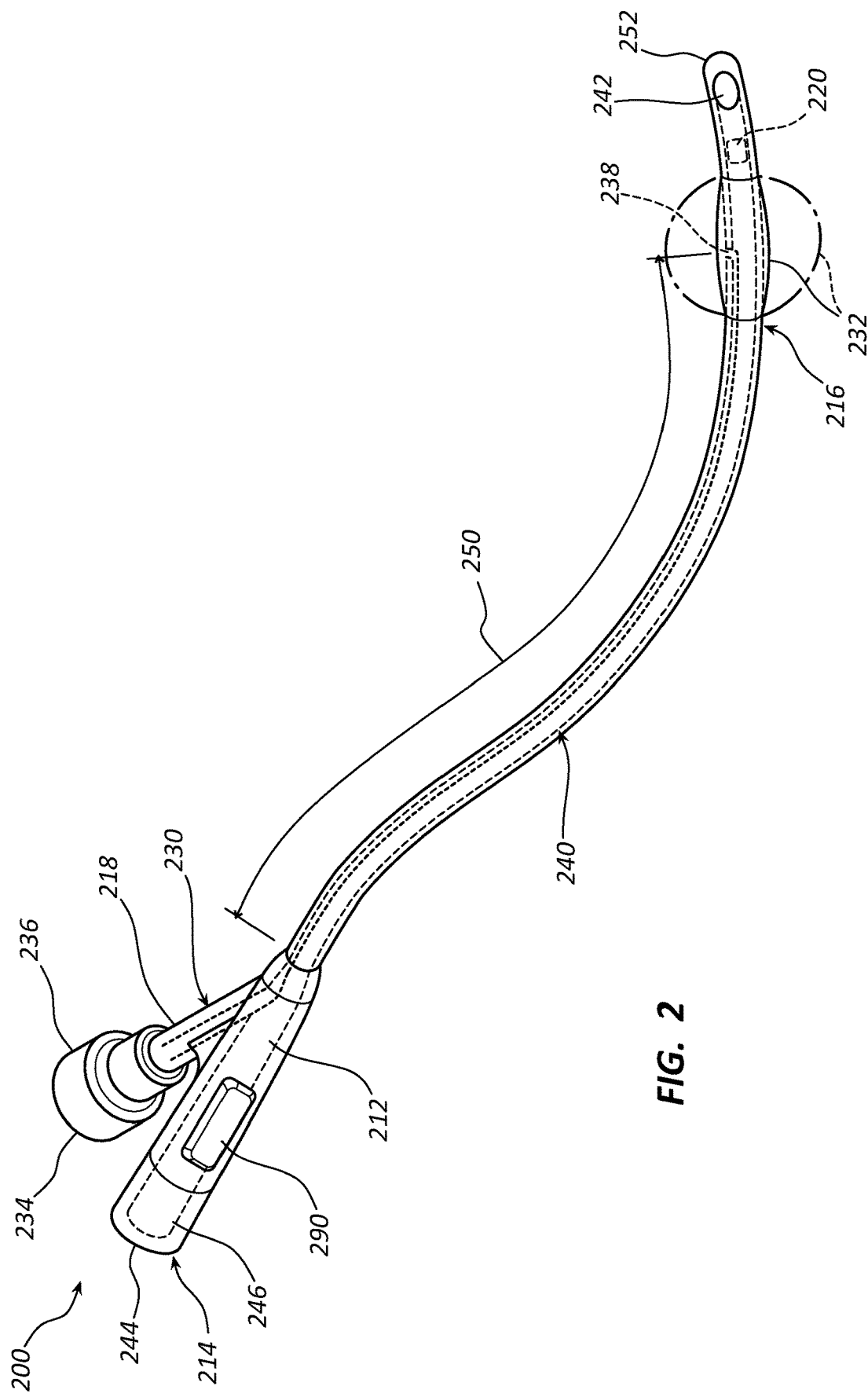

FIG. 2 provides an exemplary embodiment of a catheter in accordance with some embodiments.

Figure 3:
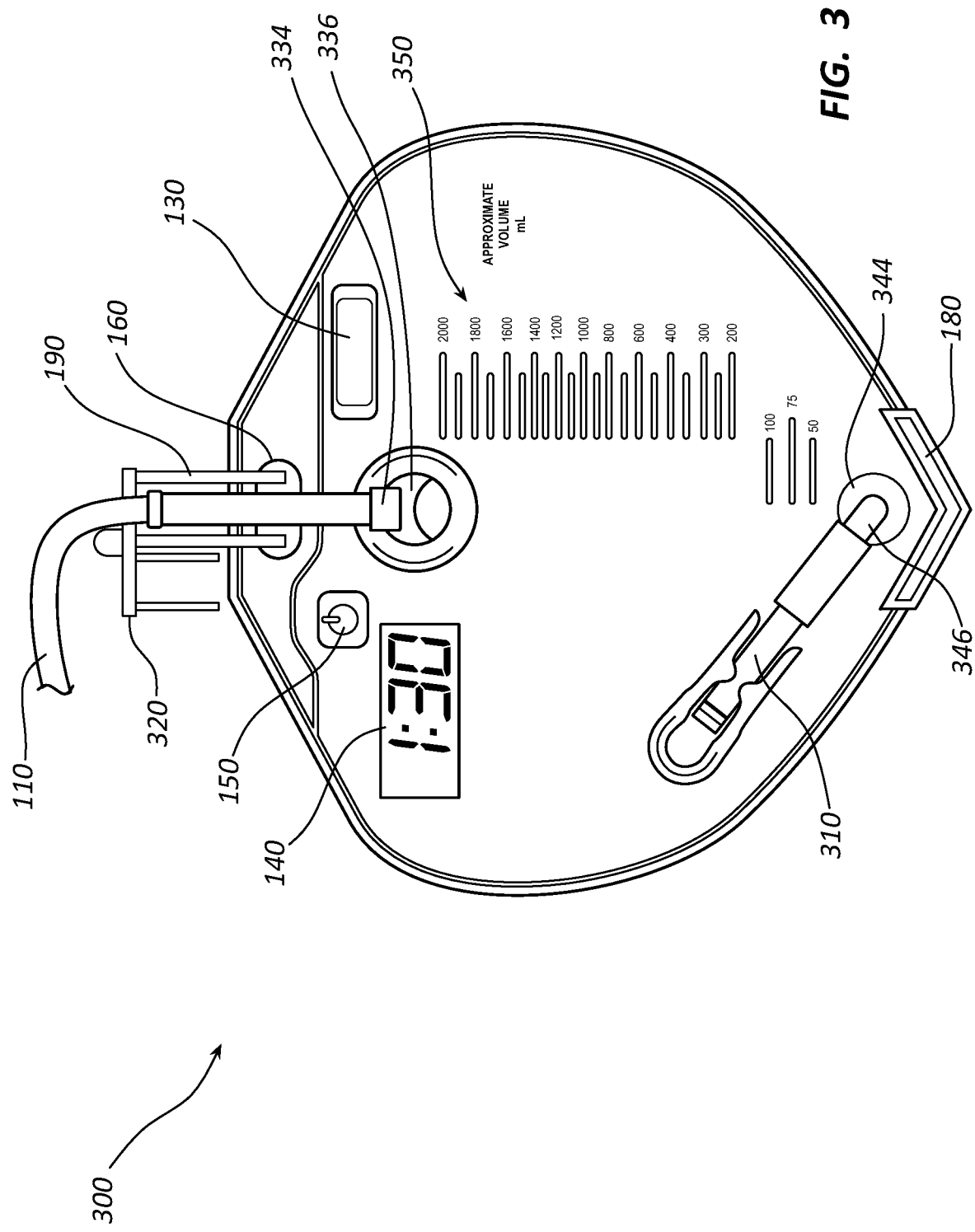

FIG. 3 provides an exemplary embodiment of a drainage bag in accordance with some embodiments.

DETAILED DESCRIPTION

Before some particular embodiments are provided in greater detail, it should be understood that the particular embodiments provided herein do not limit the scope of the concepts provided herein. It should also be understood that a particular embodiment provided herein can have features that can be readily separated from the particular embodiment and optionally combined with or substituted for features of any of a number of other embodiments provided herein.

Regarding terminology used herein, it should also be understood the terminology is for the purpose of describing some particular embodiments, and the terminology does not limit the scope of the concepts provided herein. Unless indicated otherwise, ordinal numbers (e.g., first, second, third, etc.) are used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or direction. It should also be understood that the singular forms of "a," "an," and "the" include plural references unless the context clearly dictates otherwise. Also, the words "including," "has," and "having," as used herein, including the claims, shall have the same meaning as the word "comprising."

For clarity it is to be understood that the word "proximal" as used herein refers to a direction relatively closer to a medical professional, while the word "distal" refers to a direction relatively further from the medical professional. For example, the end of a catheter placed within the body of a patient is considered a distal end of the catheter, while the catheter end remaining outside the body is a proximal end of the catheter. Unless defined otherwise, all technical and scientific terms used herein have the same meaning as commonly understood by those of ordinary skill in the art.

FIG. 1 shows an indwelling Foley catheterization system 100 which includes a catheter 200, and fluid collection or disposal equipment, such as a drainage bag 300. As used herein, a drainage bag 300 is provided for illustrative purposes; however, it will be appreciated that other examples of fluid collection or disposal equipment, including various appropriate shapes, sizes, and materials, also fall within the scope of the present invention. The catheter 200 may be fluidly connected to the drainage bag 300 by tubing 110. The tubing 110 may include various clips or attachment structures 120 which may conveniently attach excess tubing to adjacent clothing, equipment, bed rails, wheel chairs, or the like, to prevent the tubing from touching the ground or becoming entangled as the patient moves around. The catheterization system 100 may further include a stabilization device 114 which may secure a proximal end of the catheter 200 to the patient. Exemplary stabilization devices can be found in: U.S. Pat. No. 8,900,196, filed Apr. 20, 2012, and titled, "Anchoring System"; U.S. Pat. No. 9,480,821, filed Jan. 30, 2012, and titled, "Anchoring System For A Medical Article"; U.S. Pat. No. 9,642,987, filed Feb. 7, 2008, and titled, "Anchoring System For A Catheter"; and U.S. Pat. No. 9,731,097, filed Jul. 3, 2012, and titled, "Stabilizing Device Having A Locking Collet", each of which are incorporated by reference herein in their entirety.

The catheterization system 100 may further include additional equipment to facilitate the insertion and use of the indwelling catheter system. Such equipment may include lubrication, a sterile barrier, sterilization swabs, sterile gloves, instructions for use, and various other equipment for facilitating the insertion of the Foley catheter while minimizing the risk of introducing infection to the patient.

The catheterization system 100 may include one or more indicators configured to detect one or more given attributes. As used herein, it will be appreciated that the indicator may include sensors coupled with various other components necessary for the detecting, transmitting, displaying and recording of metrics which represent the one or more given attributes. It will be appreciated that the various other components necessary for the detecting, transmitting, displaying and recording of metrics may include mechanical and/or electrical components. Exemplary components may include, but are not limited to, sensors, bimetallic strips, wires, capacitors, digital displays, power sources, and the like. It will be appreciated that the indicator will include the necessary components in order to detect and indicate the one or more given attributes and are considered to fall within the scope of the present invention.

In an embodiment, the catheterization system 100 may include a location indicator 130, a duration indicator 140, an elevation indicator 150, a tamper indicator 160, a dependent loop indicator 170, a floor contact indicator 180, and a patient securement indicator 190, each of which is described in detail below. As used herein, it will be appreciated two or more of location indicator 130, duration indicator 140, elevation indicator 150, tamper indicator 160, dependent loop indicator 170, floor contact indicator 180, and patient securement indicator 190 may be combined in a single indicator apparatus. Stated differently, a single indicator apparatus may be configured to detect one or more of the given attributes detected by location indicator 130, duration indicator 140, elevation indicator 150, tamper indicator 160, dependent loop indicator 170, floor contact indicator 180, and patient securement indicator 190.

FIG. 2 shows an exemplary catheter 200 which may be used as part of the catheterization system 100. The catheter 200 may include a catheter body 212 having a proximal end 214 and a distal end 216. The distal end 216 may include a catheter tip 252 with a rounded, atraumatic end. A balloon 232 is located near the distal end 216 of the catheter adjacent the tip 252 of the catheter 200. In use, once a distal end 216 of catheter 200 is located within the bladder, balloon 232 may be inflated, using an inflation apparatus (not shown), to anchor the distal end 216 within the bladder. An exemplary inflation apparatus may include a syringe that is fluidly connected with the balloon 232 by way of an inflation lumen 230.

A drainage lumen 240 extends longitudinally within the catheter body 212 from proximal end 214 to drainage eye(s) 242 in the side wall(s) of tip 252, and is in fluid communication with drainage eye(s) 242. Although a single drainage eye 242 is illustrated, it is contemplated that the tip 252 may include multiple drainage eyes 242. Drainage eye(s) 242 permit fluid to enter the drainage lumen 240. Drainage eye(s) 242 may be burnished and polished for added smoothness to maximize patient comfort. Drainage eye(s) 242 may be relatively large holes to reduce clotting and maximize urine flow.

The proximal end 214 of the drainage lumen 240 is placed in fluid communication with fluid collection or disposal equipment, such as a drainage bag 300. The proximal end 214 of catheter 200 may include a drainage port 244 in fluid communication with the drainage lumen 240. Optionally, the proximal end 214 of catheter 200 may include a one-way drainage valve 246 that only allows fluid to drain proximally from the catheter 200, and prevents reflux of drained urine back into the catheter 200. Also, proximal end 214 of catheter 200 may include or be attached to other communication valves, chambers, funnels, or other devices through which the drainage lumen 240 communicates and/or attaches to the fluid collection or disposal equipment.

The inflation lumen 230 is formed within the wall of the catheter body 212 and extends from an inflation eye 238 inside of the balloon 232 to the proximal end 214 of catheter body 212. Catheter body 212 may include a branching arm 218 in a proximal region of the catheter body 212 through which the inflation lumen 230 passes. In use, balloon 232 is inflated once the distal end 216 of catheter 200 is positioned within a bladder of the body of the patient, which serves to anchor the distal end 216 in the bladder. The proximal end 214 of catheter 200 may include an inflation port 234 in fluid communication with the inflation lumen 230 of the catheter 200. Optionally, the proximal end 214 of catheter 200 may also include an inflation valve 236 that prevents fluid flow in the inflation lumen 230 unless the proximal end 214 is connected to a syringe or other means for inflating or deflating the balloon 232.

In an embodiment, catheter 200 may include one or more of location indicator 130, duration indicator 140, elevation indicator 150, tamper indicator 160, dependent loop indicator 170, floor contact indicator 180, patient securement indicator 190, and components thereof. By way of example, catheter 200 may include a sensor 220 located adjacent a distal end 216. Sensor 220 may be configured to detect one or more attributes, and may be communicatively coupled with one or more of location indicator 130, duration indicator 140, elevation indicator 150, tamper indicator 160, dependent loop indicator 170, floor contact indicator 180, and patient securement indicator 190 (hereinafter collectively termed "indicators 290"). One or more of indicators 290 may be disposed on the catheter body 212, adjacent a proximal end 214. In an embodiment, sensor 220 at a distal end 216 may be communicatively coupled with one or more of indicators 290 at a proximal end 214, either by way of a wire 250 disposed within a wall of the catheter body 212, or by way of a wireless connection. As used herein, wireless communications may include Bluetooth, Wi-Fi, radio, ultrasound, or similar electro-magnetic or physical (acoustic) wireless communications modes, known in the art. In an embodiment, sensor 220 may be communicatively coupled, either by wired or wireless connection, with one or more indicators 290 disposed on tubing 110, stabilization device 114, drainage bag 300, or combinations thereof. Although only a single sensor 220 is illustrated adjacent a distal end 216, it is contemplated that catheter 200 may include multiple sensors 220 located adjacent a distal end 216, a proximal end 214, within a catheter body 212, or combinations thereof.

FIG. 3 shows an exemplary fluid collection/disposal equipment, such as a drainage bag 300. Drainage bag 300 may include an inlet port 334 which may be fluidly connected to tubing 110. Optionally, inlet port 334 of drainage bag 300 may include a one-way inlet valve 336 that only allows fluid to drain into drainage bag 300, and prevents reflux of drained urine back into the tubing 110. Drainage bag 300 may further include a drainage port 344. Optionally, drainage port 344 may also include a one-way drainage valve 346 that only allows fluid to drain out of drainage bag 300, and prevents reflux of drained urine back into the drainage bag 300. Drainage port 344 may be fluidly connected to tubing 310 and associated connection structures (e.g. tap, spigot, or similar valve) that allows the drainage bag 300 to be emptied and reused if necessary.

Drainage bag 300 may include graded markings 350, used to denote volume or similar indication of the amount of fluid collected in the drainage bag 300. Drainage bag 300 may include an attachment structure 320, such as a clip, hook, or loop. The attachment structure 320 may allow the drainage bag to be attached to, or suspended from, adjacent clothing or equipment such as a belt, bedrail, wheel chair, or the like. The attachment structure 320 is configured to withstand both the weight of the drainage bag 300 as well as any fluid disposed therein.

As discussed herein, the catheterization system 100 may include one or more of location indicator 130, duration indicator 140, elevation indicator 150, tamper indicator 160, dependent loop indicator 170, floor contact indicator 180, and patient securement indicator 190, collectively termed "indicators" 290. Each of the indicators 290 may be communicatively coupled with a network. As used herein, a network may include a Local Area Network (LAN), Wireless Local Area Network (WLAN), Virtual Private Network (VPN), intranet, internet, a 'cloud' based network, or a similar centralized or decentralized, wired or wireless network which falls within the scope of the present invention. In an embodiment, each of the indicators may detect one or more given attributes and associated metrics and transmits these attributes to the network, such as an Electronic Health Record ("EHR") or Electronic Medical Record ("EMR") system, or the like. The network may then be configured to record and display these metrics.

In an embodiment, a location indicator 130 may include an apparatus for detecting a physical or geographic location of the catheterization system. The location indicator 130 may work in conjunction with various electromagnetic or magnetic fields to determine the relative position of the location indicator 130, and therefore the associated catheterization system 100, within a given area. The location indicator 130 may further record the date and time associated with the location, as well. For example, the location indicator 130 may include a Global Positioning System ("GPS") sensor configured to triangulate a relative location based off of GPS signals. Similarly, the location indicator 130 may use Wi-Fi 33 signals, GSM cellular phone signals, geomagnetic field, or similar natural or artificial, permanent or electromagnetic fields, combinations thereof, or the like, to triangulate a location. In an embodiment, the location indicator 130 may record a location at set events (e.g. when the catheter 200 was inserted, when the catheter 200 was removed), or at set time intervals (e.g. every hour, minute, or second.)

In an embodiment, the location indicator 130 may further include identification information detailing information specific to the individual device used and the patient with which it is used, or the like. Device information may include make, model, serial numbers, instructions for use, contraindications, or the like. Patient information may include, name, date of birth, medical record number ("MRN"), address, telephone number(s), specific directives, specific allergies, or the like. Such information may be communicated to the network with which the location indicator 130 is communicatively coupled. In an embodiment such information may already be stored on the network and the identification information may be linked to the device and/or patient by way of a key (e.g. serial number or MRN key) stored on the location indicator 130. It is contemplated that such identifying information may also be included with each of the indicators 290, associated with a catheterization system 100. In an embodiment, such identifying information may be included as part of a separate identification indicator (not shown), distinct from that of the indicators 290.

In an embodiment, a duration indicator 140 may detect and record real-time duration of use of a catheterization system 100. For example, the duration indicator 140 may detect and record the date and time that the catheter was inserted as well as the date and time that the catheter 200 should be replaced, in accordance with predetermined guidelines. The duration indicator 140 may include a timer, clock, or similar indicator of real-time, which may be initiated automatically at a 'start point' of use of the catheterization system 100, commonly termed 'dwell time'. For example, duration indicator 140 may be communicatively coupled with one or more sensors that may detect when a distal end 216 is disposed within a bladder, when balloon 232 has been inflated, when catheter 200 is connected to the tubing 110 and/or drainage bag 300, when urine has started to flow, or the like. One or more of these attributes may be used to by the catheterization system 100 to automatically determine a 'start point' of dwell time. Similar attributes may also be used to automatically determine an 'end point' of use or dwell time.

In embodiments, the duration indicator 140 may include a 'stopwatch' which detects and records the amount of time elapsed since a start point of use. The duration indicator 140 may include a 'timer' which measures the amount of time until an end point of use. In embodiments, different components of the catheterization system 100, e.g. catheter 200, tubing 110, drainage bag 300, may have to be replaced at different times. Stated differently, the components of the catheterization system 100 may have individual start/end points. Accordingly, the duration indicator may track separate start points, end points, and usage or dwell times for the various components of the catheterization system 100.

The duration indicator 140 may include a display configured to show the patient or medical professional the attributes detected and recorded by the duration indicator 140. The duration indicator 140 may include various audio, visual, or tactile alerts, to alert a patient or medical professional of when the catheter 200 is due to be changed, or is needing to be changed immediately. The duration indicator 140 may also alert a medical professional by way of the network, to which it is communicatively coupled as discussed herein. In an embodiment, the duration indicator 140 may include a percentage bar, progress bar, or similar graphical visual indicator of real-time.

Advantageously, the automatic initiation of the duration indicator 140 would both reduce the work load for the medical professional and remove the possibility of human error. Currently, when Foley catheters lacking a duration indicator 140 are used, a medical professional must record the date and time of when the catheter was inserted. From this, the date and time for replacing the catheter, in accordance with guidelines, may be calculated. However, if a medical professional fails to record the start date and time, or the information is lost, or communicated incorrectly, this may lead to complications. For example, the catheter may be left in place longer than is recommended, resulting in the potential malfunctions of the catheter system or an increased risk of infections due to prolonged use. Alternatively, the catheter is removed and discarded prematurely leading to an unnecessary patient discomfort from excessive exchanges of catheters, increased risk of infections during the exchange process, and increased costs for the patient due unnecessary use of equipment.

In an embodiment, an elevation indicator 150 may detect and record the elevation of drainage bag 300 relative to the bladder. In use, a catheterization system 100 may rely on a passive, gravity fed, system to maintain a correct flow of urine from the bladder to the drainage bag 300. However, if the drainage bag 300 is positioned above the bladder, urine will fail to flow correctly, creating discomfort or potentially hazardous conditions for the patient. An elevation indicator 150 may determine if the drainage bag 300 is situated correctly, below the bladder of the patient. In an embodiment, the elevation indicator 150 may work in conjunction with one or more sensors either located on the drainage bag 300, catheter 200, tubing 110, stabilization device 114, or combinations thereof, or the like. For example, a sensor 220, located adjacent a distal end 216 of the catheter 200 may determine the location of the bladder and may be communicatively coupled with an elevation indicator 150 located adjacent an inlet port 334 of the drainage bag 300. The relative positions of the elevation indicator 150 and sensor 220 may be used to determine if the drainage bag 300 is situated correctly, below the bladder. Should the elevation indicator 150 determine that the drainage bag 300 is not correctly situated, the elevation indicator 150 may alert a patient by way of a suitable audio, visual, or tactile alerts, or may alert a medical professional by way of the network, to which it is communicatively coupled as discussed herein, or combinations thereof.

In an embodiment, the elevation indicator 150 may work in conjunction with a location indicator 130. As discussed herein the location indicator 130 may include a GPS sensor, or similar sensor that is capable of determining elevation. The elevation indicator 150, location indicator 130, and associated sensors, (e.g. sensor 220), and the like, may determine the relative elevations of the bladder and drainage bag to ensure correct positioning of the drainage bag 300. In an embodiment, the elevation indicator 150 may work in conjunction with a flow sensor (not shown) disposed on a catheter 200, tubing 110, or combinations thereof. The elevation indicator 150 and flow sensor may determine the correct direction of urine flow within the catheterization system 100 and therefore determine the correct position of the bag.

In an embodiment, a tamper indicator 160 may monitor one or more of the connections within the catheterization system 100 to ensure integrity of the connections during set up and use of the catheterization system 100. The catheterization system 100 includes various fluid or electrical connections, for example, between the catheter drainage port 244 and tubing 110, between inflation port 234 and inflation apparatus, between a distal end 216 and the bladder of a patient, between the catheter 200 and stabilization device 114, between tubing 110 and inlet port 334, between one or more of the indicators 290 and the catheterization system 100, or the like. The integrity between these connections needs to be verified to ensure correct set up of the catheterization system 100. The integrity of these connections also needs to be maintained during use of the catheterization system 100. Should the connection integrity be disrupted, the system may fail to function as intended. Accordingly, the tamper indicator 160 may be communicatively coupled with one or more sensors disposed at one or more of these connections of the catheterization system to ensure the integrity of the system.

In an embodiment, the sensors of the tamper indicator 160 may use physical, electrical, magnetic, or similar modality to confirm the connection between the respective components is established correctly and maintained during use of the catheterization system 100. Should the tamper indicator 160 determine that integrity of one or more of the connections has failed, or not correctly established, the tamper indicator 160 may alert a patient by way of a suitable audio, visual, or tactile alerts, or may alert a medical professional by way of the network, to which it is communicatively coupled as discussed herein, or combinations thereof.

In an embodiment, the tamper indicator 160 may provide additional information as to the type of connection that has failed, the location of the particular failure, the particular connection within the catheterization system 100 that has failed, the individual catheterization system 100 unit that has experienced the failure, the identity of the patient with which the catheterization system 100 is associated, combinations thereof, or the like. In an embodiment the tamper indicator 160 may work in conjunction with the location indicator 130 to inform the medical professional where the patient, and associated catheterization system 100 with the failure, currently is, where the failure has occurred, or combinations thereof.

Advantageously, the tamper indicator 160 may automatically record and ensure the correct set up of the catheterization system 100, this ensures the correct implementation of the catheterization system 100 according to predetermined guidelines. Further the tamper indicator 160 may endure integrity of electrical connections between the various components to ensure the indicators 290 are all functioning correctly. The tamper indicator 160 may also ensure integrity of the fluid connections between the catheter 200, tubing 110 and drainage bag 300 which mitigates unhygienic spills and undue mess. Further, the tamper indicator 160 may allow a medical professional to monitor any patient non-compliance. For example, patients under chronic stress or having reduce mental capacity may intentionally or unintentionally interfere with the catheter system 100. In addition to creating unhygienic spills and undue mess, such actions may interfere with the gathering of important medical information and vital signs, since detecting subtle changes in urine volume and flow rate can be an important diagnosis tool. Accordingly, the tamper indicator 160 may ensure the integrity of the information recorded by the catheterization system 100, as a whole.

In an embodiment, a dependent loop indicator 170 may monitor urine pooling, dependent loops, and other flow irregularities within the catheterization system 100. As discussed herein, a fundamental aspect of catheterization systems is the monitoring of urine volume and flow rate for a patient. Complications may occur with the formation of 'dependent loops' within the catheterization system 100. Dependent loops occur when there is excess tubing 110 between the catheter 200 and drainage bags 300, creating loops of tubing. These tubing loops provide low points within a gravity fed system where urine pooling may occur. Such urine pooling may affect the volume and flow rate data recorded by the catheterization system 100. More importantly, however, such urine pooling may also lead to unhygienic conditions, and associated urinary tract infections.

The dependent loop indicator 170 may include one or more sensors associated with the catheter 200, tubing 110, drainage bag 300, or combinations thereof. The dependent loop indicator 170 may include flow rate sensors to ensure the correct direction and rate of flow of urine within the catheterization system 100. The dependent loop indicator 170 may include pressure sensors to detect the presence accumulations of static fluid within the catheterization system 100. As discussed herein, the dependent loop indicator 170 may include suitable audio, visual, or tactile alerts, or may alert a medical professional by way of the network, to which it is communicatively coupled, or combinations thereof.

As discussed herein, the catheterization system 100 may use a passive gravity feed system, or in an embodiment, the catheterization system 100 may use an active pump that moves fluid through the tubing 110 to the drainage bag. In an embodiment, the catheterization system 100 may use a combination of active and passive feed systems. Accordingly, the catheterization system 100 may predominantly rely on a gravity fed system. However, where the activity or body position of the patient is such that urine pooling occurs in tubing 110, the dependent loop indicator 170 may detect such pooling and initiate a pump to move the urine through the tubing 110 to the drainage bag 300. In this way, the catheterization system 100 may not only automatically detect the presence of a dependent loop and urine pooling, but may also rectify the problem automatically, without the need for intervention from a medical professional or patient.

In an embodiment, a floor contact indicator 180 may monitor whether the catheterization system 100, or components thereof, is touching or has touched a floor surface. The floor contact indicator 180 may work in conjunction with one or more sensors disposed on the drainage bag 300, tubing 110, catheter 200, or combinations thereof. In use, the drainage bags of catheterization systems are often attached to a waist belt on the patient, or to a bed rail, wheel chair, or similar piece of equipment adjacent the patient. During the initial set up of the catheterization system, the empty drainage bag may seem securely attached to the belt or equipment. However, as the bag fills with fluid and increases in weight, the attachment may become insufficient leading to the drainage bag slipping and touching or dragging along the floor. If such a situation goes unnoticed by the patient or busy medical professional, it can lead to various functional or hygienic problems, including for example, the wearing or rupturing of the drainage bag.

In an embodiment, a floor contact indicator 180 may include a sensor disposed on a lower portion of the drainage bag 300. Should the drainage bag 300 slip and make contact with a floor surface, the floor contact indicator 180 may alert a patient or medical professional either by way of suitable audio, visual, or tactile alerts, or may alert a medical professional by way of the network, to which it is communicatively coupled, or combinations thereof. In an embodiment, a floor contact indicator 180 may include sensors disposed at other key points within the catheterization system 100 which may indicate a portion of the catheterization system 100 is, or has touched, the floor. For example, a sensor may be located between the drainage bag 300 and attachment structure 320. Accordingly, when any part of the drainage bag 300 makes contact with the floor, not just a lower most point substantially at floor contact indicator 180, a sudden drop in pressure detected at attachment structure 320 may indicate the drainage bag is touching the floor.

In an embodiment, a floor contact indicator 180 may include sensors disposed on tubing 110. For example a collar 182 may be slidably coupled with tubing 110, such that the collar 182 will automatically align with a lower most point along the tubing 110. Should the lower most point of the tubing 110 come into contact with the floor, a floor contact indicator 180, or sensor communicatively coupled therewith, disposed on collar 182 may detect the contact and alert the patient or medical professional as discussed herein. It will be appreciated that, as illustrated, collar 182 may be part of the dependent loop indicator 170. Alternatively, collar 182 may be a separate structure from the dependent loop indicator 170.

In an embodiment, a floor contact indicator 180 may include sensors that detect various attributes in order to determine if a portion of the catheterization system 100 is, or has, made contact with the floor. For example, sensors may detect pressure, three-dimensional ("3D") spatial location, velocity or force (e.g. gyroscopic sensors, accelerometers), distance (e.g. using infrared, laser, or acoustic modalities), proximity (e.g. using radar, motion, magnetic force), combinations thereof, or the like. Similarly, the floor contact indicator 180 may work in conjunction with one or more of indicators, such as the location indicator 130, elevation indicator 150, or the like, to determine if a portion of the catheterization system 100 is, or has, made contact with the floor. In an embodiment, the floor contact indicator 180 may include sensors capable of determining if a portion of the catheterization system 100 is about make contact with the floor and provide a warning to the patient or medical professional, as described herein, so that contact between the floor and catheterization system 100 may be averted.

In an embodiment, a patient securement indicator 190 may monitor whether the catheterization system 100, or a component thereof, is attached to the patient, or has been detached therefrom. The catheterization system 100 may be secured to a patient at various points; for example, drainage bag 300 may be secured to the patient using attachment structure 320 and a proximal end 214 of the catheter 200 may be secured to the skin of the patient using stabilization device 114. As discussed herein, various problems may occur if the catheterization system 100, or a component thereof, becomes detached from the patient, either intentionally or unintentionally. For example, the detached portion may become disconnected from the catheterization system 100, the portion may drag on the floor or become entangled. Such situations may result in damage to the catheterization system 100 or unsanitary conditions, leading to an increased risk of infection.

In an embodiment, a patient securement indicator 190 may include one or more sensors that may detect if one or more portions of the catheterization system 100 is secured to the patient. As discussed herein, the sensors may use various modalities to determine if the catheterization system 100, or a portions thereof, are secured to the patient. Such modalities may include, electromagnetic, magnetic, pressure, force, velocity, combinations thereof, or the like. Similarly, the patient securement indicator 190 may work in conjunction with other indicators, such as the location indicator 130, floor contact indicator 180, or the like, to determine if the catheterization system 100, or portion thereof, has become detached from the patient. As discussed herein, should the catheterization system 100, or portion thereof, become detached from the patient, the patient securement indicator 190 may provide suitable audio, visual, or tactile alerts to a patient, or may alert a medical professional by way of the network, to which it is communicatively coupled, or combinations thereof.

In an exemplary method of use, a catheterization system 100 may be provided including a catheter 200, drainage bag 300, tubing 110, and one or more of location indicator 130, duration indicator 140, elevation indicator 150, tamper indicator 160, dependent loop indicator 170, floor contact indicator 180, and patient securement indicator 190. The catheterization system 100 may further include additional equipment to facilitate the insertion and use of the indwelling catheter system. Such equipment may include lubrication, a sterile barrier, sterilization swabs, sterile gloves, instructions for use, and various other equipment for facilitating the insertion of the Foley catheter while minimizing the risk of introducing infection to the patient.

For urinary catheters such as Foley catheters, the catheter 200 is introduced into the patient and is advanced into the patient's urethra until the distal end 216 of the catheter 200, including the balloon 232, resides within the bladder. The balloon 232 is then inflated, typically by coupling a syringe to the proximal end 214 of the catheter 200 such that the syringe may communicate with the inflation lumen 230, and actuating the syringe to discharge fluid from the syringe, through the inflation lumen 230, and into the balloon 232. To remove a catheter 200, it is first necessary to deflate the balloon 232 anchoring the distal end 216 of the catheter 200. This is done by withdrawing fluid through the inflation lumen 230, typically through a syringe coupled to the inflation lumen 230 via inflation valve 236 and inflation port 234.

The balloon 232, which in one embodiment is made of an elastomeric material, is positioned around the catheter shaft. The balloon 232 is preferably engineered to retain its shape once inflated without significantly deforming due to pressures arising while within the body. The balloon 232 may include ribs (e.g., thicker polymer portions or added reinforcement) to ensure strength and symmetry of the material.

With the distal end 216 of the catheter 200 located within the bladder of the patient, a proximal end 214 may be secured to the skin of the patient using a stabilization device 114. Tubing 110 may then fluidly connect the catheter 200 with the drainage bag 300. The drainage bag 300 may be secured at an appropriate position relative to the bladder of the patient. The one or more indicators 290 may automatically detect when the catheterization system 100 is correctly deployed. For example, the indicators 290, may automatically detect and record: the individual patient with which the specific catheterization system 100 is being used; when the distal end 216 of the catheter is correctly located within the bladder; when the balloon is correctly inflated; when a proximal end 214 of the catheter 200 is secured to the patient; when a proximal end 214 of the catheter 200 is connected to the tubing 110; when the tubing 110 is connected to the drainage bag 300; when drainage bag 300 is secured to the patient; when urine flow commences; when drainage bag 300 is full; when catheterization system 100, or components thereof, need to be replaced according to predetermined guidelines; and when catheterization system 100 is removed from the patient.

The indicators 290 of the catheterization system 100 may also detect and record the location of the catheterization system 100 when various events occur, as discussed above, or at various time intervals throughout the use of the catheterization system 100, or combinations thereof. The indicators 290 of the catheterization system may also detect and record any faults that may occur during the usage of the catheterization system 100, such as: a misalignment of the drainage bag 300 relative to the bladder of the patient; a connection integrity failure of within the catheterization system 100; a dependent loop or flow irregularity within the tubing 110; any contact between the catheterization system 100 and a floor surface; or any detachment of the catheterization system 100, or portion thereof, from the patient during the use of the catheterization system 100.

The information detected and recorded by the catheterization system 100 may be stored locally on a non-transitory storage device associated with the catheterization system 100, or may be stored remotely to a network, as discussed herein. The catheterization system 100 may continue to be used until a predetermined end point has been reached. The predetermined end point may determine by a specific date and time, by a specific amount of time that has elapsed, by a specific amount of fluid that has been collected, or when a specific event or fault has been detected, combinations thereof, or the like.

While the invention has been described in terms of particular variations and illustrative figures, those of ordinary skill in the art will recognize that the invention is not limited to the variations or figures described. For example, specific examples are provided for shapes and materials; however, embodiments include those variations obvious to a person skilled in the art, such as changing a shape or combining materials together. Further, the features described with respect to one embodiment or variation may be used in other embodiments or variations. Processes described separately may be combined. In addition, where processes and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A catheter, comprising:
   a catheter body, having a proximal end and a distal end;
   a balloon disposed adjacent to the distal end;
   a drainage lumen extending from the distal end to the proximal end;
   an inflation lumen extending from the balloon to the proximal end; and
   a sensor disposed adjacent to the distal end and communicatively coupled with an indicator disposed in an external wall of the catheter body adjacent to the proximal end opposite a branching arm of the catheter body through which the inflation lumen passes.

2. The catheter according to claim 1, wherein the sensor and the indicator are communicatively coupled by way of a wire disposed in a wall of the catheter body.

3. The catheter according to claim 1, wherein the sensor and the indicator are communicatively coupled by means of wireless communication.

4. The catheter according to claim 1, wherein the sensor is designed to detect at least one of: an internal body temperature, a presence of moisture, a pressure, a three-dimensional spatial location, a velocity of the catheter, a force on the catheter, a distance of the catheter to an object, or a proximity of the catheter to the object.

5. The catheter according to claim 4, wherein the indicator is designed to communicate with the sensor to indicate an attribute relating to at least the three-dimensional spatial location, the presence of moisture, an inflation of the balloon, the velocity of the catheter, the force on the catheter, the proximity of the catheter to the object, the distance of the catheter to the object, or the internal body temperature.

6. The catheter according to claim 5, wherein the sensor is designed to detect the force on the catheter and the indicator is a patient securement indicator.

7. The catheter according to claim 4, wherein the indicator is selected from the group consisting of: a location indicator, a duration indicator, an elevation indicator, a tamper indicator, a dependent loop indicator, a floor contact indicator, or a patient securement indicator.

8. The catheter according to claim 7, wherein the sensor is designed to detect a start point of dwell time and an end point of dwell time and the duration indicator is designed to indicate a real time duration of use of the catheter.

9. The catheter according to claim 8, wherein the start point of dwell time includes when the distal end is disposed within a bladder, when the balloon has been inflated, or when urine has started to flow through the catheter.

10. The catheter according to claim 7, wherein the sensor is designed to detect the three-dimensional spatial location of the catheter and the indicator is the location indicator.

11. The catheter according to claim 1, wherein the sensor is a pressure sensor designed to detect a presence of accumulations of static fluid and the indicator is a dependent loop indicator.

* * * * *